United States Patent
Jang

(10) Patent No.: US 11,737,956 B2
(45) Date of Patent: Aug. 29, 2023

(54) COMPOSITION FOR INTRACANAL MEDICATION

(71) Applicant: MARUCHI, Wonju-si (KR)

(72) Inventor: Sung Wook Jang, Seoul (KR)

(73) Assignee: MARUCHI

( * ) Notice: Subject to any disclaimer, the term of this patent is extended or adjusted under 35 U.S.C. 154(b) by 874 days.

(21) Appl. No.: 16/462,581

(22) PCT Filed: Nov. 21, 2017

(86) PCT No.: PCT/KR2017/013298
§ 371 (c)(1),
(2) Date: Jul. 9, 2019

(87) PCT Pub. No.: WO2018/093239
PCT Pub. Date: May 24, 2018

(65) Prior Publication Data
US 2020/0060947 A1     Feb. 27, 2020

(30) Foreign Application Priority Data

Nov. 21, 2016  (KR) .................. 10-2016-0155276

(51) Int. Cl.
| | |
|---|---|
| *A61K 6/00* | (2020.01) |
| *A61K 6/853* | (2020.01) |
| *A61K 6/54* | (2020.01) |
| *A61K 6/76* | (2020.01) |
| *A61K 6/869* | (2020.01) |
| *A61K 6/73* | (2020.01) |
| *A61K 6/69* | (2020.01) |
| *A61K 6/56* | (2020.01) |
| *A61K 6/80* | (2020.01) |

(52) U.S. Cl.
CPC ............... *A61K 6/853* (2020.01); *A61K 6/54* (2020.01); *A61K 6/56* (2020.01); *A61K 6/69* (2020.01); *A61K 6/73* (2020.01); *A61K 6/76* (2020.01); *A61K 6/80* (2020.01); *A61K 6/869* (2020.01)

(58) Field of Classification Search
CPC . A61K 6/853; A61K 6/73; A61K 6/69; A61K 6/54; A61K 6/76; A61K 6/56; A61K 6/80; A61K 6/869
See application file for complete search history.

(56) References Cited

U.S. PATENT DOCUMENTS

| | | | |
|---|---|---|---|
| 5,635,162 A | 6/1997 | Fischer | |
| 6,585,514 B2 | 7/2003 | Imai et al. | |
| 10,154,945 B2 * | 12/2018 | Jang | C04B 22/0093 |
| 2012/0191214 A1 * | 7/2012 | Nies | A61L 27/40 |
| | | | 623/23.62 |
| 2013/0023601 A1 | 1/2013 | Ogliari et al. | |
| 2014/0050674 A1 * | 2/2014 | Tjaderhane | A61K 6/50 |
| | | | 424/49 |

FOREIGN PATENT DOCUMENTS

| | | | | |
|---|---|---|---|---|
| JP | 2012-77025 A | | 4/2012 | |
| KR | 20150100446 A | | 9/2015 | |
| KR | 1020150100446 A | * | 9/2015 | |
| WO | 2009/029049 A1 | | 3/2009 | |
| WO | 2012/146832 A2 | | 11/2012 | |
| WO | WO-2016124679 A1 | * | 8/2016 | ............... A61K 6/17 |

* cited by examiner

*Primary Examiner* — Michael P Cohen
(74) *Attorney, Agent, or Firm* — Dinsmore & Shohl LLP

(57) ABSTRACT

The present invention relates to a composition of an intracanal medication agent for medicating root canals for a predetermined period of time. According to one aspect of the invention, there is provided an intracanal medication composition based on a calcium hydroxide component, comprising: calcium hydroxide or a calcium hydroxide producing component as a powder component; and at least one of diethyl sulfoxide (DMSO), N-methyl-2-pyrrolidone (NMP) and diethylene glycol monoethyl ether (DEGEE) as a liquid component.

10 Claims, 5 Drawing Sheets

COMPOSITION FOR INTRACANAL MEDICATION

CROSS-REFERENCE TO RELATED APPLICATION(S)

This application is a continuation application of Patent Cooperation Treaty (PCT) international application Serial No. PCT/KR2017/013298, filed on Nov. 21, 2017, which claims priority to Korean Patent Application Serial No. 10-2016-0155276, filed on Nov. 21, 2016. The entire contents of PCT international application Serial No. PCT/KR2017/013298 and Korean Patent Application Serial No. 10-2016-0155276 are hereby incorporated by reference.

FIELD OF THE INVENTION

The present invention relates to a composition of an intracanal medication agent for medicating root canals for a predetermined period of time. The intracanal medication agent may prevent invasion or growth of bacteria in root canals, and may inhibit formation of apical lesions by neutralizing bacterial endotoxins.

BACKGROUND

When bacteria invade into a tooth to cause infection and reduce the vitality of pulp tissues, the tooth is subjected to a series of treatment processes in which the pulp tissues are removed and the infected area is sterilized, and then sealing is performed to prevent secondary infection. The above processes are called endodontic treatment.

Although endodontic treatment has a relatively high success rate when inflammation does not spread to the deep part of pulp cavity, the success rate is lowered when the deep part of the pulp cavity is already infected or the apical region is even infected. Further, the success rate of retreatment is sharply lowered when infection occurs again in a tooth that has undergone endodontic treatment.

Important factors in disinfection and sterilization of the interior of a root canal are to prevent infection and inflammation by the removal of infected soft tissues and the effective removal of a smear layer generated during the formation of the root canal and a biofilm present in the infected root canal. Since the internal anatomy of a tooth is diverse and varied, users (mostly dentists) will use various cleaning agents and medication agents (to be described later) for chemical disinfection as well as physical removal, in order to remove the infected tissues in the root canal.

Sodium hypochlorite (NaOCl) is widely used for disinfection and cleaning of the interior of a root canal, and is effective in dissolving soft tissues and removing a biofilm. (Further, sodium hypochlorite has strong antibacterial activity and can even dissolve living tissue residues and remove organic materials of dentinal tubules.) However, it cannot be easily applied to the depths of the root canal since it has a low viscosity and surface tension, and its effect cannot be sustained since it is rapidly neutralized in the root canal. Particularly, it is not much of help in removing a smear layer. The biofilm and smear layer described herein are in the form of membranes. Unlike the smear layer in which soft tissues are simply tangled with removed hard tissue fragments resulting from a mechanical removing process, the biofilm is attached to hard tissues with lipopolysaccharides.

A medication inserted and maintained in a root canal for a predetermined period of time to inhibit bacterial growth and neutralize bacterial endotoxins is referred to as a medication agent. Over a long period of time, calcium hydroxide medication agents have been selected by users. The calcium hydroxide agents are well-tested and safe, and may be used in combination with sodium hypochlorite. Calcium hydroxide is a safe compound that has been used in human bodies for a long time. Although calcium hydroxide is hardly soluble in water, it increases the acidity of water to pH 12.4 even with a very small amount of dissolution (at this time, it is dissociated into calcium ions and hydroxyl ions), thereby causing chemical burning and obtaining antibacterial activity.

Such a calcium hydroxide medication agent may include calcium hydroxide itself, but may also include calcium oxide or a calcium silicate compound (e.g., a calcium disilicate compound or a calcium trisilicate compound) which produces calcium hydroxide through a hydration reaction.

From the viewpoint of endodontic treatment, the effects and characteristics of calcium hydroxide are as below.

(1) Antibacterial and Antifungal Properties

Hydroxyl ions produced when calcium hydroxide is ionized have a strong effect on some biomolecules, and particularly can damage cell membranes, denature proteins, or damage DNA in bacteria.

(2) Neutralization of Bacterial Endotoxins

Bacterial endotoxins are components in cell walls of bacteria, and typically include polysaccharides, lipids, proteins, and the like. They cause inflammation and alveolar bone uptake, and play important roles in the formation, maintenance, and enlargement of apical lesions. It is known that such bacterial endotoxins can be neutralized by calcium hydroxide medication agents.

(3) Action on a Biofilm

It is known that toxicity in a root canal is actually caused by a biofilm, which is an aggregate of bacteria, rather than by individual bacteria. A biofilm including *E. faecalis* in the root canal is a significant challenge to users. However, no medication agent is yet known to effectively act against such a biofilm, and conventional calcium hydroxide medication agents are still in use but their effects are doubtable.

(4) Induction of Hard Tissue Formation

The use of a calcium hydroxide medication agent may induce the formation of hard tissues damaged by apical inflammation or the like.

(5) Contrast with Other Materials

In addition to sodium hypochlorite, chlorhexidine (CHX), MTAD, ethylenediaminetetraacetic acid (EDTA), and citric acid are frequently used for cleaning purposes. However, in the case of CHX, there is a problem that it inherently has a less protective effect against bacterial invasion than calcium hydroxide, and when it is used with sodium hypochlorite, it chemically reacts therewith to produce toxic precipitates, discolor a dental root, and compromise the effectiveness of an intracanal medication agent. Further, MTAD also has a problem of losing its antibacterial activity due to an acid-base reaction with sodium hypochlorite. Furthermore, a corrosive solution such as EDTA and citric acid or a cleaning agent including at least one of the foregoing has a problem, when used with sodium hypochlorite, of destroying collagen and hydroxyapatite, which are the main anatomical structures of a dental root, to weaken the dental root and melting the entrances of dentinal tubules to deteriorate the root canal sealing, if the time of usage is prolonged or the order of usage is wrongly arranged.

Therefore, in consideration of the above, it seems that calcium hydroxide is most suitable to be used for the purpose of intracanal medication together with sodium hypochlorite.

However, there is a problem that it is very inconvenient to push a powdered calcium hydroxide medication agent product into a root canal, and when water is used as a solvent, the mixture is easily dried to deteriorate manipulability. For example, there is even a phenomenon that the calcium hydroxide medication agent is early stiffened within a syringe.

Due to the above problems, at least one selected from a group consisting of glycerol, polyethylene glycol, polypropylene glycol, propylene glycol and the like has been often used as a solvent. Particularly, in order to prevent hardening within a syringe for user convenience, a glycol having a high viscosity and good moisture retention has been adopted as a solvent for a calcium hydroxide medication agent. However, although such a calcium hydroxide medication agent provides relatively more user convenience due to its less surface drying, it has a drawback in that it inherently has excessively low antibacterial activity since it lowers the solubility of calcium hydroxide, and it is not cleanly removed afterward. The remnants resulting from the insufficient removal may cause various problems such as providing a pathway for bacterial infection later, lowering the solubility of residual pulp tissues or biofilms relative to sodium hypochlorite, and inhibiting the diffusion of hydroxyl ions into the dentin.

Although an idea of using antibiotics and the like (e.g., ciprofloxacin) together has been suggested to solve problems such as infection, this has caused toxicity problems while favorably inducing the elimination of a biofilm.

Accordingly, the inventor(s) have developed a novel and inventive intracanal medication composition that is excellent for use in intracanal medication and comprises calcium hydroxide or a component producing calcium hydroxide through a hydration reaction.

SUMMARY OF THE INVENTION

One object of the present invention is to solve all the above-described problems in the prior art.

Another object of the invention is to provide a novel and inventive calcium hydroxide intracanal medication agent.

Yet another object of the invention is to provide an intracanal medication agent that is highly antibacterial, easily removable, and safe without causing a toxic reaction in a human body.

The representative configurations of the invention to achieve the above objects are described below.

According to one aspect of the invention, there is provided an intracanal medication composition based on a calcium hydroxide component, comprising: calcium hydroxide or a calcium hydroxide producing component as a powder component; and at least one of dimethyl sulfoxide (DMSO), N-methyl-2-pyrrolidone (NMP) and diethylene glycol monoethyl ether (DEGEE) as a liquid component.

In addition, there are further provided other intracanal medication compositions to implement the invention.

According to the invention, it is possible to provide a novel and inventive calcium hydroxide intracanal medication agent.

According to the invention, it is possible to provide an intracanal medication agent that is highly antibacterial, easily removable, and safe without causing a toxic reaction in a human body.

DETAILED DESCRIPTION

Figure 1:
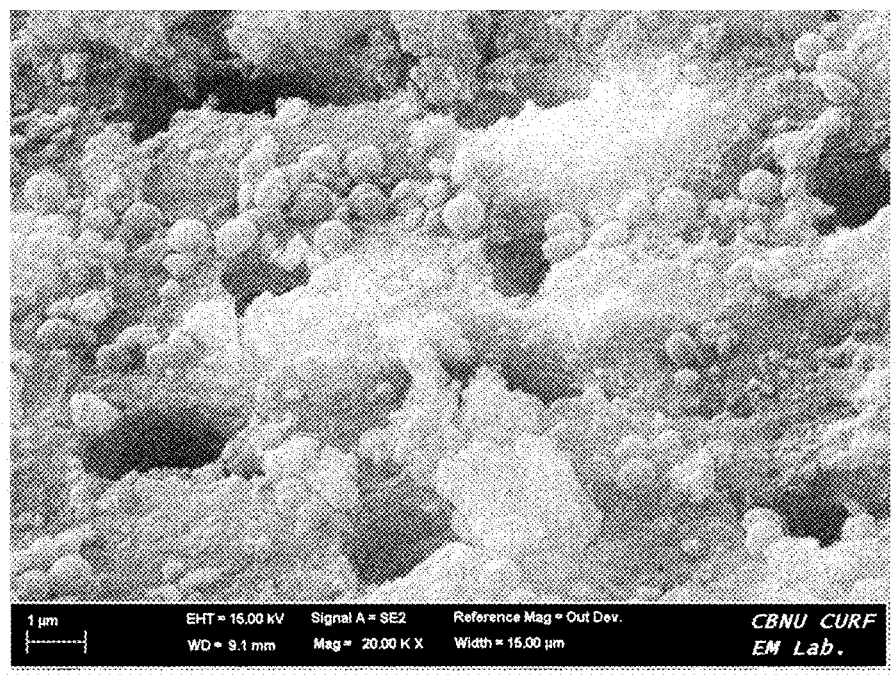
FIGS. 1 to 6 are comparative photomicrographs.
Figure 2:
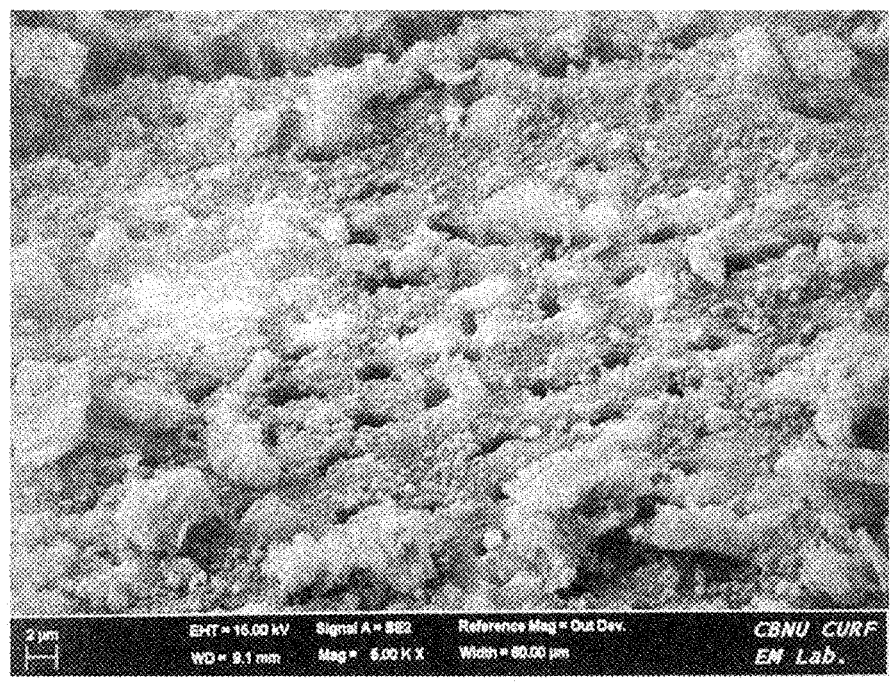

In the following detailed description of the present invention, references are made to the accompanying drawings that show, by way of illustration, specific embodiments in which the invention may be practiced. These embodiments are described in sufficient detail to enable those skilled in the art to practice the invention. It is to be understood that the various embodiments of the invention, although different from each other, are not necessarily mutually exclusive. For example, specific shapes, structures, components, and characteristics described herein may be implemented as modified from one embodiment to another without departing from the spirit and scope of the invention. Furthermore, it shall be understood that the locations or arrangements of individual elements within each of the embodiments, or the conditions or orders of the mixtures, reactions and the like of the individual elements, may also be modified without departing from the spirit and scope of the invention. Therefore, the following detailed description is not to be taken in a limiting sense, and the scope of the invention is to be taken as encompassing the scope of the appended claims and all equivalents thereof. In the drawings, like reference numerals refer to the same or similar elements throughout the several views.

Hereinafter, various preferred embodiments of the present invention will be described in detail with reference to the accompanying drawings to enable those skilled in the art to easily implement the invention.

PREFERRED EMBODIMENTS OF THE INVENTION

An intracanal medication agent according to one embodiment of the invention may comprise calcium hydroxide or a component producing calcium hydroxide through a hydration reaction, and a stripping agent having strong penetrability. The intracanal medication agent will be described in detail below.

(1) Calcium Hydroxide or a Component Producing Calcium Hydroxide Through a Hydration Reaction The intracanal medication agent may include calcium hydroxide to an extent allowed in a human body, or a component that produces calcium hydroxide through a hydration reaction (e.g., calcium oxide). Such components may be provided in the form of powder. It is preferred that the particle size of calcium hydroxide or calcium oxide is small since the reaction with water (e.g., water in the human body) is facilitated as the particle size is smaller. However, the viscosity of the intracanal medication agent is increased when the particle size is smaller than tens of nanometers, which is unfavorable when it is necessary to remove the intracanal medication agent afterward.

The component that produces calcium hydroxide when mixed with water may include Portland cement or pozzolan cement that mainly consists of calcium silicate compounds. The inventor(s) already hold several patents (or patent applications) with respect to various inventions in which such cement has been developed for dentistry, either on their own or through their affiliated companies. A list of the patents applications is given below.

TABLE 1

| No. | Applicant | Inventor(s) | KR Appl. No. | Title of invention |
|---|---|---|---|---|
| 1 | JANG, Sung Wook | JANG, Sung Wook | 10-2008-0038387 | Pozzolan cement for dental treatment |
| 2 | Maruchi Co., Ltd. | JANG, Sung Wook | 10-2012-0028458 | Dental filling composition comprising zirconia powder |
| 3 | JANG, Sung Wook | JANG, Sung Wook | 10-2013-0112165 | Dental filling composition comprising zirconia powder |
| 4 | Maruchi Co., Ltd. | JANG, Sung Wook LIM, Ho Nam KIM, Eui Seong OH, Sei Jin | 10-2014-0032686 | Dental hydraulic filler composition of single paste type |
| 5 | Maruchi Co., Ltd. | JANG, Sung Wook CHO, Kye Hong CHO, Jin Sang CHOI, Moon Kwan MOON, Ki Yeon | 10-2014-0122694 | Hydraulic binder composition having ultra-rapid hardening property |

It should be considered that the contents of the listed patent applications are incorporated herein by reference in their entirety.

Accordingly, those skilled in the art may prepare the component required for the intracanal medication agent according to one embodiment of the invention, i.e., the component producing calcium hydroxide through a hydration reaction, by using or slightly applying the techniques disclosed in the above patent applications.

In the case of Portland cement, it reacts with water to produce hydrous calcium silicate and calcium hydroxide, which may be less preferred because a considerable part of the surface after hardening tends to be occupied by calcium hydroxide. Thus, it may be more preferred to include a pozzolanic material that may convert calcium hydroxide on the surface after hardening to hydrous calcium silicate which is stable and neutral in the human body.

(2) Stripping Agent

It may be preferred that a stripping agent liquid, which is particularly crucial for the invention, has the following properties:

It can be used in a human body.
It can be mixed with a strongly basic material.
It has a low viscosity and does not interfere with the diffusion of hydroxyl ions (produced by calcium hydroxide reacted with water) into dentinal tubules and the like, so that they function like hydroxyl radicals.

It mixes with water easily and facilitates permeation.

The low viscosity of the stripping agent may have a significant meaning when the intracanal medication agent according to one embodiment of the invention is removed after fulfilling a predetermined function. This is because if the temporarily applied agent is not removed well, interference may be caused and the effectiveness of treatment may also be reduced. The stripping agent with a low viscosity may assist the intracanal medication agent to be removed by simply being flushed with water.

Further, the permeation facilitation of the stripping agent may be helpful in view of complex anatomical structures within root canals. This may obviously reduce reliance on unwieldy instruments.

Dimethyl sulfoxide (DMSO), N-methyl-2-pyrrolidone (NMP) and diethylene glycol monoethyl ether (DEGEE) may be all considered as excellent stripping agent liquids that fulfill the above properties.

In order to mix such a stripping agent with calcium hydroxide to peel off a bacterial biofilm or smear layer in a root canal, it may be preferred that a combination including one or more selected from the above stripping agent liquids accounts for not less than 70% of the total weight of the solution.

The stripping agent may permeate with hydroxyl ions. Due to this strong permeation mechanism, the stripping agent may permeate deep into the smear layer, which covers a dentinal tubule surface with clumping of removed dentin fragments and soft tissues, and may act at an interface between the smear layer and the root canal to assist the smear layer to be washed off together with the intracanal medication agent according to one embodiment of the invention when the intracanal medication agent is washed off later. Further, the stripping agent may permeate the interior of the dentinal tubules below the interface to cause strong antibacterial activity against parasitic bacteria within the dentinal tubules. The effects of the stripping agent may also include solving a problem that when the smear layer is removed with EDTA or citric acid (which has been used in the field of endodontic treatment) and then the exposed dentinal tubules and their interior are disinfected again with sodium hypochlorite, the exposed dentinal tubules are melted again and clogged.

By using a mixture of a stripping agent and a calcium hydroxide component, it is possible to acquire a mechanism of an antibiotic such as ciprofloxacin, which produces hydroxyl radicals to cause strong antibacterial activity against a biofilm.

Meanwhile, water may or may not be additionally included. However, when DMSO is employed, a small amount of water may be an effective component that can drastically lower the freezing point of the DMSO.

Further, all of the above three liquids may be used to properly dissolve polysaccharides. The polysaccharides are major components of bacterial endotoxins and play important roles in causing biofilms to adhere to living tissues, and thus dissolving the polysaccharides can be an important advantage.

(3) Viscosity Enhancing Agent

According to one embodiment of the invention, a viscosity enhancing agent may be further included.

It has been often difficult to remove a conventional intracanal medication agent after application when necessary. It is known that the intracanal medication agent that has been applied in an endodontic treatment process should be cleanly removed so that disinfection and sealing may be performed subsequently. However, it requires a lot of time and effort to remove a conventional calcium hydroxide medication agent mixed with a high viscosity liquid such as propylene glycol, polyethylene glycol and polyvinyl pyrrolidone.

However, the above-described stripping agent such as DMSO has a viscosity as low as water and is easily removed, while it is difficult for a user to apply the intracanal medication agent into the root canal due to the excessively low viscosity. Accordingly, it may be necessary to include a suitable viscosity enhancing agent so that the intracanal medication agent may be easily removed and have an appropriate viscosity. Further, it may be preferred that the viscosity enhancing agent is readily soluble in water and does not affect the ionization of calcium hydroxide.

The viscosity enhancing agent may comprise at least one of cellulose derivatives such as methyl cellulose, hydroxyethyl cellulose, hydroxypropyl methylcellulose (HPMC), and carboxymethyl cellulose.

Further, the viscosity enhancing agent may comprise at least one of polyols such as xylitol, erythritol and sorbitol. This may improve ease of use by lowering the freezing point of the stripping agent. Further, its inherent anti-biofilm effect may also contribute to the purpose of intracanal medication.

Erythritol having an excellent anti-biofilm effect may be a preferred polyol. Particularly, it may be most effective when it is included in a weight ratio of about 5% to 9% with respect to DMSO. That is, 9% or more of erythritol may increase the viscosity excessively, and 5% or less of erythritol may have an excessively weak effect in lowering the freezing point.

Further, a viscosity enhancing agent that may be appropriately viscous and easily washed off, such as clay or synthetic clay belonging to a smectite group (i.e., expandable phyllosilicates including bentonite, hectorite and the like) may also be employed even though it is not water-soluble. Due to the proper combination of solubility and insolubility in water, such a viscosity enhancing agent may expand and disperse the intracanal medication agent that has become stiff in the root canal during a cleaning process, so that the intracanal medication agent may be more easily removed. Particularly, clay such as bentonite that inherently has strong antibacterial activity may impart more strong antibacterial activity to the intracanal medication agent. Such swelling clay may further increase the removal effect as the rate of expansion in water is larger than that in a state where the swelling clay is kneaded in a storage solvent.

Further, a viscosity enhancing agent such as water-soluble chitin and a chitosan derivative may also be used.

Although the viscosity enhancing agent may increase the removal effect as it is added in a greater amount, it may preferably be included in an amount of 10% or less by weight with respect to the weight of calcium hydroxide, in order to achieve a proper viscosity. It may be more effective to use a suitable combination of the above viscosity enhancing agents according to the choice of those skilled in the art, rather than use only one of them.

(4) Radiopaque Material

According to one embodiment of the invention, a radiopaque material may be further included for radiation reading. (This material may be provided in the form of powder). For example, at least one of barium sulfate, zirconium oxide, bismuth oxide, tantalum oxide, and calcium tungstate may be used. Further, bismuth titanate or barium titanate may also be used alone or in combination with other materials.

For high levels of radiopacity and biocompatibility, it may be preferred to use ferroelectric materials such as bismuth titanate or barium titanate, or zirconium oxide which is safe in vivo.

It may be preferred that the radiopaque material is included in an amount of 20 to 55 wt % with respect to the entire composition. However, when the ratio of the radiopaque material is slightly higher than that allowed by the international standards, it may be more readily determined whether the medication agent in a root canal has been surely removed.

Meanwhile, the radiopaque material itself may function as a laundry ball during a cleaning process, which may assist the separated smear layer or biofilm to be washed out of the root canal. For this action, it may be preferred to add a relatively lighter material such as zirconium oxide or barium titanate, rather than a relatively heavier material such as bismuth titanate, in an amount by weight similar to or greater than that of calcium hydroxide.

Therefore, compared with a conventional calcium hydroxide medication agent in which a low content of calcium hydroxide is mixed with an existing high viscosity liquid, the intracanal medication agent according to one embodiment of the invention may have a sufficient content of calcium hydroxide (i.e., at least in an amount by weight of 30% or more of the weight of the entire intracanal medication agent), so that the radiopaque material may be added in an amount sufficient to substantially assist the cleaning.

(5) Exemplary Method of Application

The above-described intracanal medication agent according to one embodiment of the invention may be applied by the following method. However, it is noted that the method is described only for illustration.

The intracanal medication agent according to one embodiment of the invention may act strongly when it is in direct contact with a smear layer or biofilm. However, since a user cannot know in advance whether the smear layer or biofilm is present throughout a root canal or in a specific site thereof, it may be important to fill the intracanal medication agent according to one embodiment of the invention in the entire root canal, if possible.

However, it is not economical to fill all the formed root canal with the intracanal medication agent, and there is a risk that the intracanal medication agent may be excessively pushed into apical tissues over the apical region during a process of injecting the intracanal medication agent up to the root canal length. Particularly, although calcium hydroxide is hardly soluble in water, it may cause chemical damage even with only a small amount. When chemical damage is given to inferior alveolar nerves, mental nerves and the like below mandibular molars or premolars, there is a risk that it may lead to a permanent sensory disorder.

Therefore, it is very important to apply the intracanal medication agent to the entire root canal wall such that the intracanal medication agent is not pushed out of the root apex.

In order to solve this problem, it is necessary to employ an intracanal medication method that is different from a method for injecting an intracanal medication agent into a root canal using a conventional plastic tip. However, it is not clinically effective to employ a method that is more complicated or cumbersome than those usually employed by dentists for this purpose.

Thus, according to one embodiment of the invention, it is possible to inject the intracanal medication agent to about the middle one-third of the root canal and then slowly push in a gutta-percha cone to the root canal length so that the intracanal medication agent is applied up to the root apex. Thereafter, a radiograph is taken to confirm that the intracanal medication agent has been correctly inserted up to the root apex, which may be performed in conjunction with a process of inserting a gutta-percha cone and taking a radiograph to measure the root canal length according to a conventional endodontic treatment protocol. That is, conventionally, a radiograph for identifying the root canal length is taken after inserting only a gutta-percha cone in the root canal with nothing else being inserted therein, whereas according to one embodiment of the invention, there is only a small difference that the radiograph is taken after inserting a gutta-percha cone in the root canal with the intracanal medication agent being inserted therein, which may allow the intracanal medication agent to be evenly applied up to the root canal length, and additionally, may provide a preliminary process for more precise endodontic treatment by enabling practice in a later process of permanently sealing the root canal.

(6) Preparation Examples

The intracanal medication agent according to one embodiment of the invention may have the following content ratio. It is noted that the content ratio is illustrative.

(Preparation Example 1) The intracanal medication agent may be prepared by mixing NMP, calcium hydroxide, zirconium oxide, and hydroxypropyl methylcellulose. In this case, the weight ratio may be 36:30:30:4.

(Preparation Example 2) The intracanal medication agent may be prepared by mixing DMSO, calcium hydroxide, zirconium oxide, and hydroxypropyl methylcellulose. In this case, the weight ratio may be 36:30:30:4.

(Preparation Example 3) The intracanal medication agent may be prepared by mixing DMSO, calcium hydroxide, zirconium oxide, bentonite, and hydroxypropyl methylcellulose. In this case, the weight ratio may be 33:30:30:2:5.

(Preparation Example 4) The intracanal medication agent may be prepared by mixing DMSO, calcium hydroxide, zirconium oxide, erythritol, and bentonite. In this case, the weight ratio may be 28:30:30:7:5.

The radiopacity of the intracanal medication agents prepared according to Preparation Examples as above corresponded to 4 mm or more of an aluminum step wedge according to the ISO standards, which is higher than that allowed by the international standards. In the above, the weight ratio of calcium hydroxide was fixed at 30%.

Preparation Examples 1 to 4 will be further discussed with reference to the drawings.

FIGS. 1 to 6 are comparative photomicrographs.

FIG. 1 shows a SEM (Scanning Electron Microscope) photograph of an existing product called Apexical, and FIG. shows the Apexical SEM photograph at a different magnification. Apexical is known as a calcium hydroxide agent including polyethylene glycol.

Figure 3:
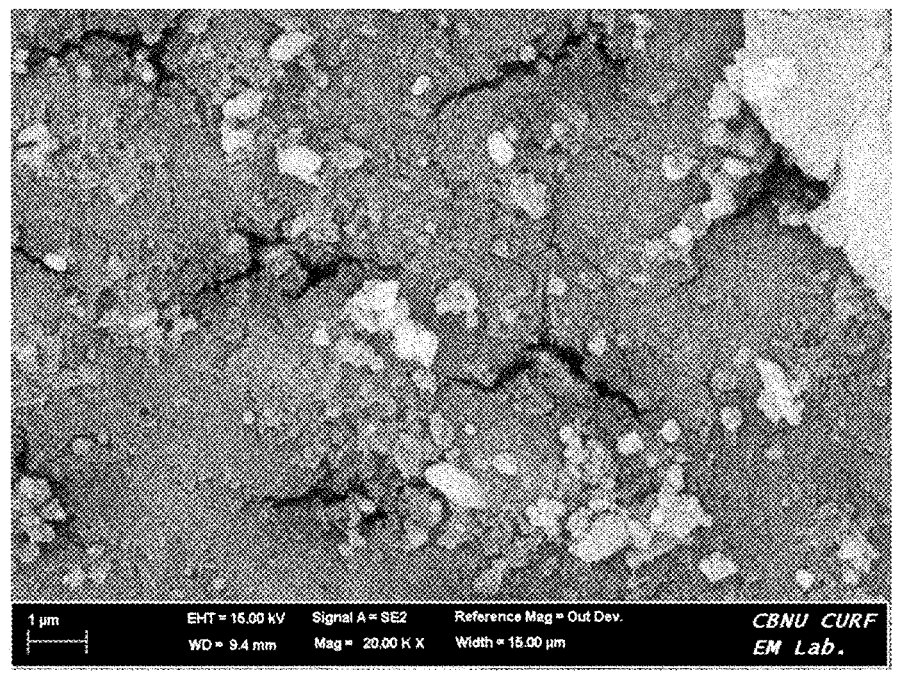
Figure 4:
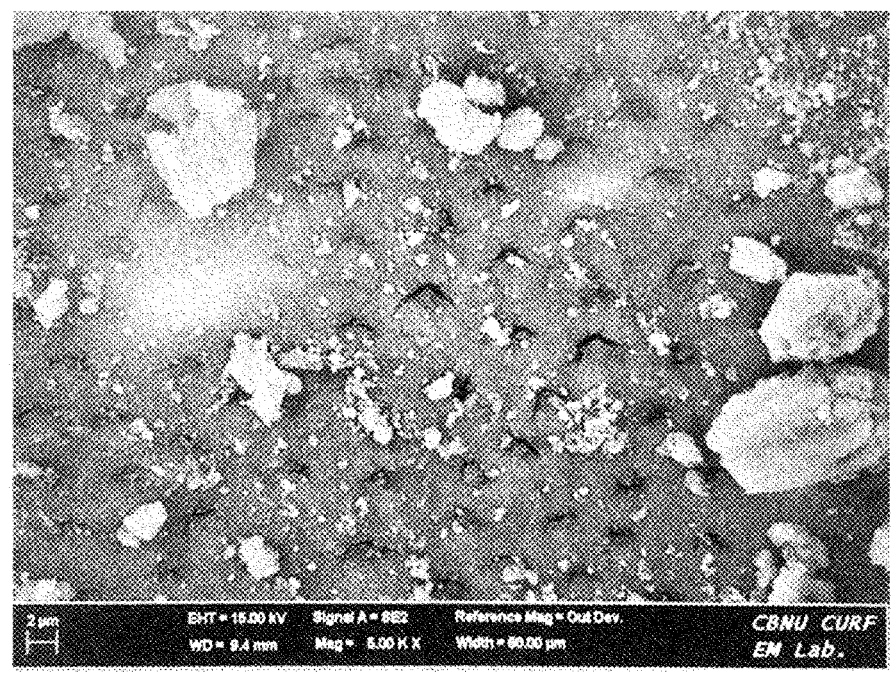

FIG. 3 shows a SEM photograph of an existing product called Calcipex, and FIG. 4 shows the Calcipex SEM photograph at a different magnification. Calcipex is known as a calcium hydroxide agent including propylene glycol.

Figure 5:
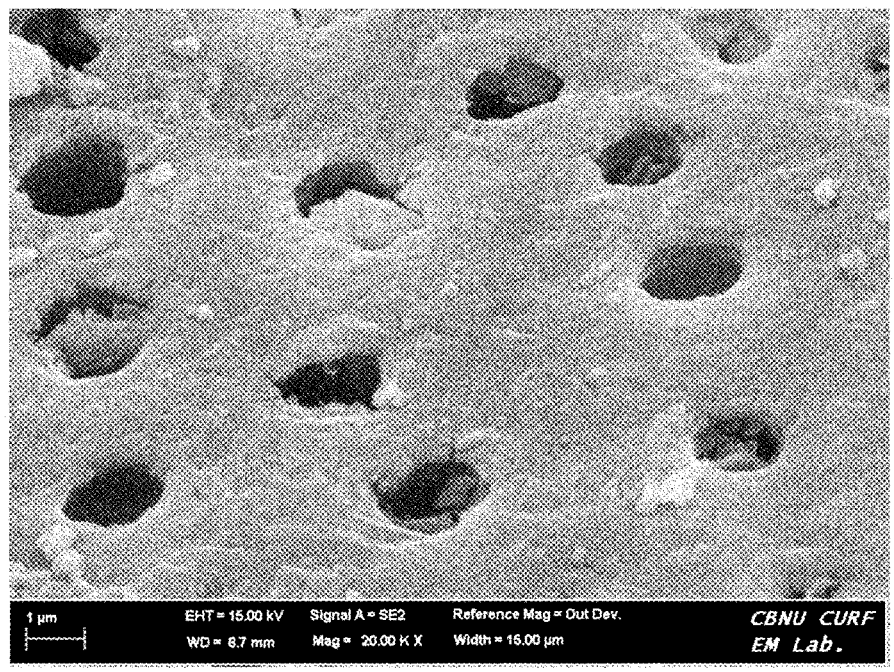
Figure 6:
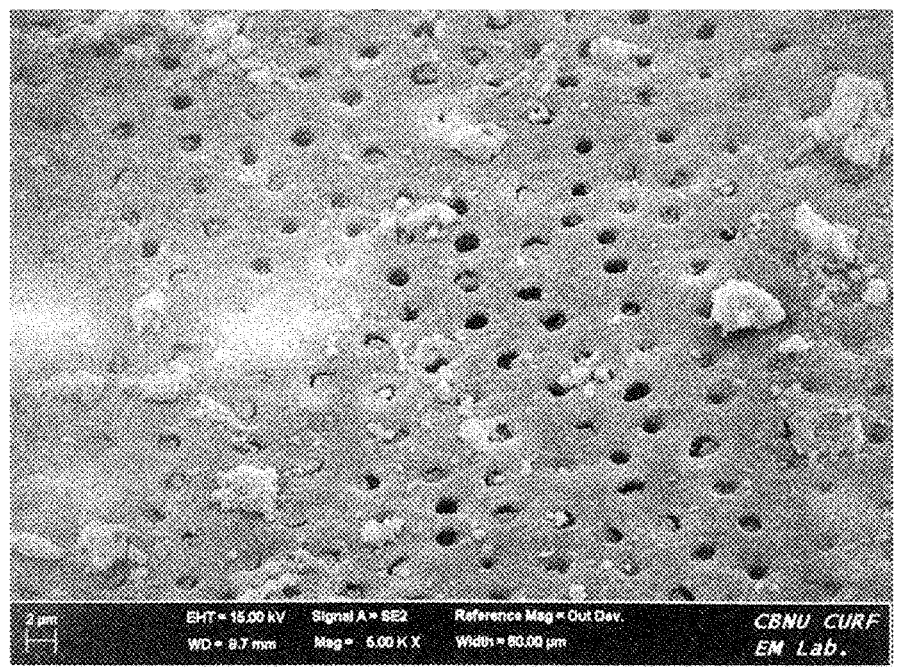

FIGS. 5 and 6 show SEM photographs of the specimen according to Preparation Example 1 of the invention. (Similarly, the photographs are shown at different magnifications).

According to one of the most common test methods for observing a smear layer in the field of endodontic treatment, a root canal was formed in a bovine tooth using a dental root canal file, and the specimens of FIGS. 1 to 6 were applied for one week. Thereafter, mechanical cleaning was performed with physiological saline and then SEM photographs were taken and observed. As shown, it can be seen that the smear layer still blocks dentinal tubules in FIGS. 1 to 4 and bacteria are present in FIGS. 1 and 2. On the other hand, it can be seen that the smear layer blocking the dermal tubules is nearly removed and almost no bacteria are present in FIGS. 5 and 6.

Figure 7:
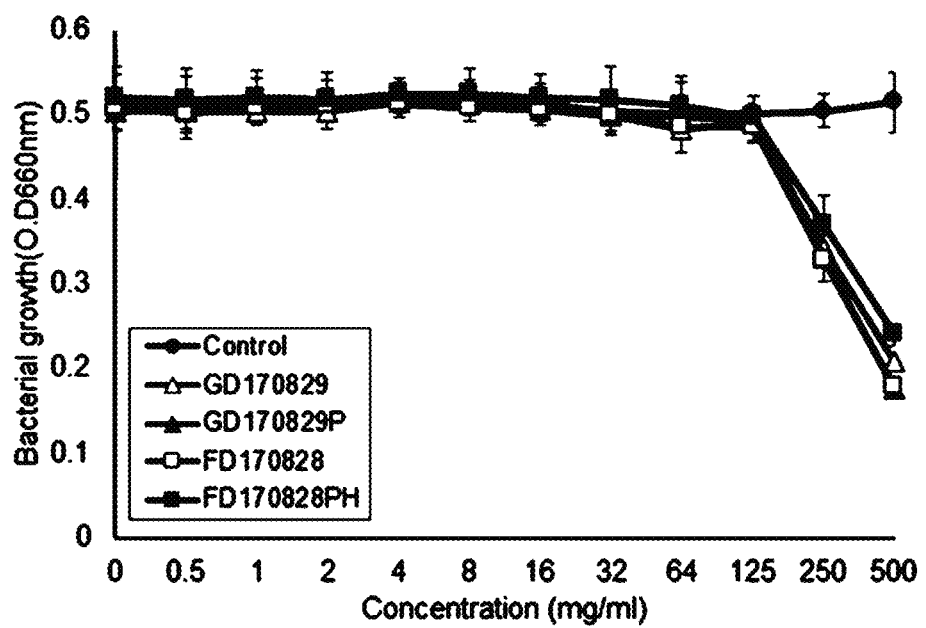
FIG. 7 is a graph showing a situation in which specimens according to Preparation Examples 2 and 3 to be described below are applied to *E. faecalis* having a biofilm, respectively.

FIG. 7 is a graph showing a situation in which the specimens according to Preparation Examples 2 and 3 are applied to E. faecalis having a biofilm, respectively. FIG. is a graph showing a situation in which the specimens according to Preparation Examples 2 and 3 are applied to P. endodontalis having a biofilm, respectively.

Figure 8:
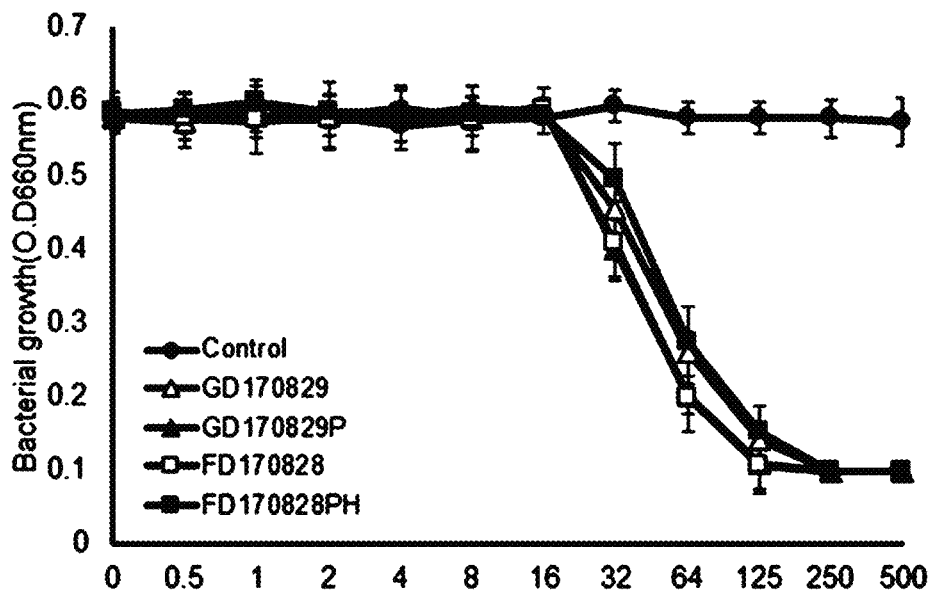
FIG. 8 is a graph showing a situation in which the specimens according to Preparation Examples 2 and 3 are applied to *P. endodontalis* having a biofilm, respectively.

In FIGS. 7 and 8, Preparation Example 2 is identified as GD170829 and Preparation Example 3 is identified as GD170829P. The description of the other two specimens will be omitted for convenience.

For the tests of FIGS. 7 and 8, as bacteria, E. faecalis ATCC 29221 was cultured at 37° C. in an aerobic condition using a brain heart infusion (BHI) medium (BD bioscience, Sparks, Md., USA) and P. endodontalis ATCC 35406 was cultured at 37° C. in an anaerobic condition (5% of $H_2$, 10% of $CO_2$ and 85% of $N_2$) using a brain heart infusion liquid medium containing 1 µg/ml of hemin and 0.2 µg/ml of vitamin K.

First, E. faecalis was inoculated on a 12-well plate and cultured for one week in an anaerobic state, while the existing liquid medium was removed and replaced with a fresh liquid medium by 1 ml on every day. The medium was removed after one week and then 0.5 mg of GD170829 and GD170829P were applied and allowed to stand at 37° C. in an anaerobic state for 2 hours. Then, 1 ml of a BHI liquid medium was added and the biofilm was removed with a scrapper. 2 ml of suspension was transferred to a tube and centrifuged at 1,000×g for 10 minutes to remove sample particles. Supernatant containing the bacteria was transferred to a clean tube. Thereafter, the suspension containing the bacteria was diluted 10-fold and inoculated in a BHI solid medium, and then the number of the bacteria was measured. In order to measure the number of the bacteria, a method of measuring absorbance at a wavelength of 660 nm using a micro-reader was used.

In addition, the above process was performed for P. endodontalis in a similar manner.

As a result, it can be seen that the anti-biofilm effect was excellent in both cases of FIGS. 7 and 8, as shown.

Figure 9:
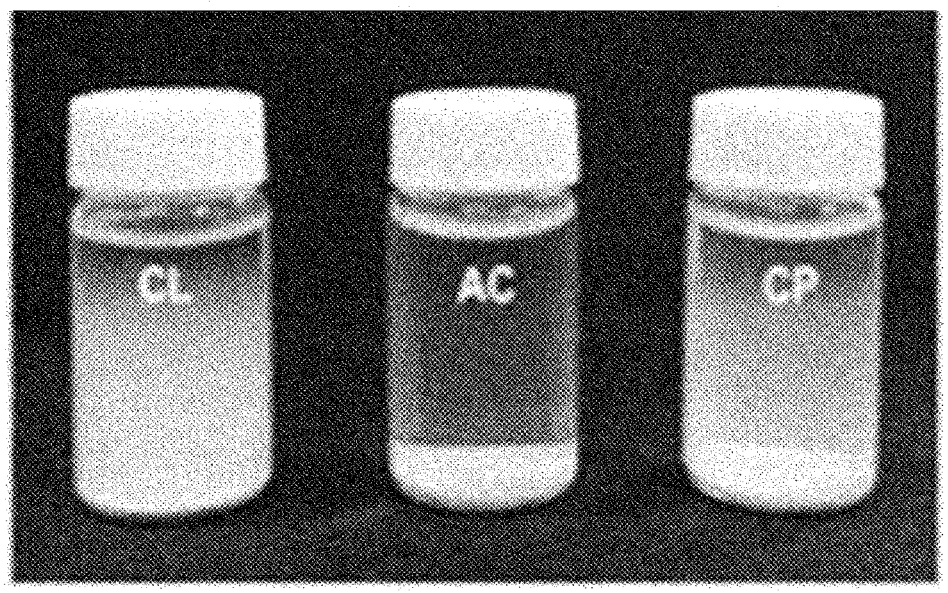
FIG. 9 is a photograph for comparing the turbidity of a suspension of a specimen according to Preparation Example 1 to be described below with that of suspensions of other specimens.

FIG. 9 is a photograph for comparing the turbidity of a suspension of the specimen according to Preparation Example 1 with that of suspensions of the other specimens. Here, CL represents the specimen according to Preparation Example 1, AC represents the specimen of Apexical, and CP represents the specimen of Calcipex II. Since the specimen according to Preparation Example 1 had fewer sediments and the suspension thereof was in good condition, it is apparent that the specimen may be easily removed.

What is claimed is:

1. A method for treating a root canal using a calcium hydroxide component-based composition as intracanal medication, wherein the composition comprises:
calcium hydroxide or a calcium hydroxide producing component as a powder component; and
at least one of dimethyl sulfoxide (DMSO), N-methyl-2-pyrrolidone (NMP) and diethylene glycol monoethyl ether (DEGEE) as a liquid component,
wherein the at least one of the DMSO, NMP and DEGEE is included at 70% or more of weight of liquid components of the composition, and wherein the method comprises the steps of:

injecting the composition into a root canal such that the at least one of the DMSO, NMP and DEGEE acts in conjunction with hydroxyl ions produced by the calcium hydroxide to peel off a biofilm or smear layer in the root canal; and removing the composition from the root canal after a predetermined period of time.

2. The method of claim 1, wherein the composition further comprises a viscosity enhancing agent.

3. The method of claim 2, wherein the viscosity enhancing agent comprises a cellulose derivative.

4. The method of claim 3, wherein the cellulose derivative comprises at least one of methyl cellulose, hydroxyethyl cellulose, hydroxypropyl methylcellulose, and carboxymethyl cellulose.

5. The method of claim 2, wherein the viscosity enhancing agent comprises a polyol.

6. The method of claim 5, wherein the polyol comprises at least one of xylitol, erythritol, and sorbitol.

7. The method of claim 2, wherein the viscosity enhancing agent comprises at least one of bentonite, hectorite, and swelling clay.

8. The method of claim 2, wherein the viscosity enhancing agent comprises at least one of water-soluble chitin and a chitosan derivative.

9. The method of claim 1, wherein the composition further comprises a radiopaque material as the powder component.

10. The method of claim 9, wherein the radiopaque material comprises at least one of barium sulfate, zirconium oxide, bismuth oxide, tantalum oxide, calcium tungstate, bismuth titanate, and barium titanate.

\* \* \* \* \*